United States Patent [19]  [11] 4,128,641
Itil  [45] Dec. 5, 1978

[54] TETRACYCLIC PSYCHOTROPIC DRUG

[75] Inventor: Turan M. Itil, Tarrytown, N.Y.

[73] Assignee: HZI Research Center Inc., Tarrytown, N.Y.

[21] Appl. No.: 772,663

[22] Filed: Feb. 28, 1977

Related U.S. Application Data

[63] Continuation-in-part of Ser. No. 600,597, Jul. 31, 1975, abandoned.

[51] Int. Cl.² ............................................. A61K 31/495
[52] U.S. Cl. ..................................................... 424/250
[58] Field of Search ........................................ 424/250

[56] References Cited
U.S. PATENT DOCUMENTS 3,534,041  10/1970  Van Der Bury et al. .... 260/268 PC

OTHER PUBLICATIONS

Drug Information Association, May 1972, p. 5.

*Primary Examiner*—Stanley J. Friedman

[57] ABSTRACT

A method of treating patients having a psychiatric condition such as schizophrenia, or having an anxiety syndrome or other neurosis, comprising administering to such patient a therapeutically effective amount of a compound having the formula

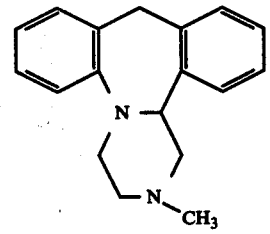

10 Claims, No Drawings

TETRACYCLIC PSYCHOTROPIC DRUG

CROSS-REFERENCE TO RELATED APPLICATION

This application is a continuation-in-part of application Ser. No. 600,597, filed July 31, 1975, now abandoned.

BACKGROUND OF THE INVENTION

This invention relates to a new use for the drug mianserin or GB-94, which belongs to a group of compounds known broadly as "tetracyclics," and more particularly to the discovery of the marked effectiveness of this drug when employed as a pharmacologically active agent in the treatment of psychoses such as schizophrenia and neuroses such as anxiety syndrome.

Mianserin is represented by the following structural formula:

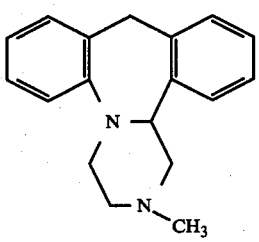

The invention further relates to the use of the pharmacologically active compound, mianserin and its use as an antipsychotic (neuroleptic) and antianxiety (anxiolytic) agent. For the sake of clarity, brevity and ease of understanding, the compound will hereinafter be referred to as GB-94 (this designation appears in the literature, for instance Proceedings of a Symposium on Depressive Illness and Experiences with a New Antidepressant Drug GB-94, editor T. Vossenaar — Excerpta Medica).

Several years ago a group of "tetracyclic" compounds was developed by structural modification of the phenbenzamine molecule for use as antiserotonin and antihistamine drugs. In the animal, one of these compounds namely GB-94 was found to have particularly potent peripheral antihistamine-antiserotonin properties. This activity was confirmed in clinical trials using patients having allergic conditions, hay fever, asthma and migraine. However as the clinical trials did not demonstrate that GB-94 had any advantages over existing antiallergic drugs, the clinical use of this tetracyclic as an antiallergic drug was discontinued.

The subsequent search for potent antiserotonin compounds with minimal side effects to use in the treatment of manic patients, resulted in a renewed interest in these tetracyclics.

In order to determine whether the tetracyclic compound GB-94 had any significant CNS effects, a single rising dose tolerance study utilizing quantitative EEG was carried out. The results of this study established that:

1. GB-94 produces marked CNS effects as indicated by significant EEG alterations. Generally these changes are characterized by a decrease of alpha activity and a concomitant increase of slow and very fast beta activity. However, it was observed that in some subjects there was a marked increase of slow waves and decrease of fast activities in both the primary wave and first derivative measurements of the computer analysis. On the other hand, in other subjects, there was a decrease of the slow waves and an increase of the frequencies in the range of 20-40 cps in both the primary wave and first derivative measurements of digital computer period analysis.

2. The type of EEG alterations induced by GB-94 were, in some subjects, strikingly similar to those changes induced by antipsychotic (neuroleptic) compounds and in other subjects similar to those changes induced by the minor tranquilizers (anxiolytics).

Several biologically active derivatives of the piperazine are already known. Thus, U.S. Pat. No. 2,794,804 describes piperazines substituted at both nitrogen atoms and in the ring by a lower alkyl or hydroxyalkyl group. These compounds possess an oral vasodilating activity and exert an inhibiting action on adrenergic activity. U.S. Pat. No. 3,037,983 describes many other derivatives in which the two nitrogen atoms are substituted and in which a methyl group occurs in the nucleus, in α-position relative to the nitrogen atoms which also are possessed of an inhibitory effect on adrenergic activity.

In U.S. Pat. No. 3,534,041 related to similar derivatives, it is noted that the compounds of the piperazine type "...possess an oral vasodilating activity and exert an inhibiting action on adrenergic effect"... "have a dilating activity on the bronchi and are usable in the treatment of asthma." GB-94 (mianserin) which is included in the patent is described as exerting an anti-inflammatory, antiserotonic and antihistaminic, as well as a strong antiphlogistic activity. It is apparent that the latter patent teaches that only the corresponding intermediate precursors possess any antidepressive and tranquilizing activity. It is totally unexpected and highly surprising that antipsychotic (neuroleptic) and anxiolytic (minor tranquilizers) properties are present in the final product. Antiserotonins and antihistamines as a general rule do not exhibit anxiolytic and neuroleptic activities. It was only possible by utilizing the quantitative EEG, more specifically quantitative pharmacoelectroencephalography (QPEEG) TM to establish the anxiolytic and neuroleptic properties of GB-94. Recently, the validity of quantitative pharmaco-EEG as a predictive method for psychotropic drugs was demonstrated (Itil, T. M., et al. Quantitative pharmaco-electroencephalography using frequency analyzer and digital computer methods in early drug evaluations; Smith, W. L., Drugs, Development and Brain Functions. Springfield, Ill, Charles C. Thomas, 1971, pp. 69-80). Using the QPEEG techniques, not only have the psychotropic properties of a series of compounds as predicted by animal pharmacology been confirmed, but more important as in the case of GB-94 it has become possible to predict the psychotropic properties of compounds for which such activity previously could not have been predicted by animal pharmacology (Itil, T.M. Quantitative pharmaco-electroencephalography in the discovery of a new group of psychotropic drugs, Diseases of the Nervous System, 33(8):557-559, 1972).

SUMMARY OF THE INVENTION

It is, accordingly, an object of this invention to provide for anxiolytic (minor tranquilizer) and antipsychotic (neuroleptic) uses for GB-94 (Mianserin) as referred to above.

These properties of GB-94 were predicted solely on the basis of computer EEG (CEEG TM) profiles of GB-94 for this compound as demonstrated by quantitative pharmaco-EEG methods.

It is still another object of the invention to provide for such a drug, which drug, however, does not have the pharmacological and neurochemical properties of existing anxiolytics and neuroleptics.

These and other objects of the invention will become more apparent as the description proceeds hereinafter.

Broadly speaking, the instant invention includes the provision of a method of treating patients with psychotic reactions such as seen in schizophrenia and anxiety syndromes such as seen among other neuroses by administering to them an effective dosage of GB-94 (Mianserin) represented by the structural formula referred to above. GB-94 (Mianserin) is, accordingly, useful in the treatment of psychotic patients with thought disorders, perceptual distortion, aggressive episodes of agitation, hostility such as seen in schizophrenia, in acute and chronic organic brain syndromes, alcohol psychosis, psychosis after addictive drugs (heroin, amphetamines, etc.), childhood psychoses, psychosis in epilepsy, and psychoses with toxic (exogenous) origin and the like conditions. It was observed that the antipsychotic (neuroleptic) effect of GB-94 occurs predominantly in higher dosages of this compound (more than 40 mg. daily). Most interestingly, GB-94 does not produce the well-known side effects, such as the extrapyramidal side effects (Parkinson-like behavior, tremor, akathisia, dystonic reactions, oculogyric crisis, tardive dyskinesia, etc.) which occurs during treatment with almost all well-known antipsychotic drugs (neuroleptics). Extrapyramidal system side effects are not seen after administration of GB-94 even in the highest daily dosages (400 mg.). Furthermore, GB-94 is effective in treating patients with anxiety associated with neuroses, psychoses, affective disorders, alcoholism, drug abuse, personality disorders, psychophysiological conditions, premenstrual syndrome, behavior disturbances of childhood and adulthood, and in related disorders. Since GB-94 (Mianserin) does not relate structurally to the well-known anxiolytics (such as benzodiazepines) nor does it pharmacologically possess the profile of the "classical" anxiolytics (minor tranquilizers), it is expected that it will not have the "addictive" properties associated with the known anxiolytics. As is well known, the anxiolytics are not yet classified as "classical" addictive compounds, but are widely misused possibly due to the development of a "dependency" on these drugs. It is expected that GB-94 will provide a source for an anxiolytic having neither "dependency" nor "addictive" properties.

DETAILED DESCRIPTION

The method for preparing GB-94 is known in the art and need not be repeated herein. Any suitable method for the synthesis of such tetracyclic compound will serve for the preparation of GB-94 in sufficient quantity and purity. More particularly, the methods of preparation are set forth in detail in U.S. Pat. Nos. 3,534,041 and 3,701,778, the disclosures of which are incorporated herein by reference.

The compounds can be administered orally, as powders or tablets, in the form of suppositories, by intramuscular or subcutaneous injections, and as sniff powder, for example, in the form of sprays, in doses between 10–400 mg a day.

The compound may be applied as drugs, for example, in the form of pharmaceutical preparations. For that purpose, they are mixed with one or more pharmaceutical vehicles suitable for oral administration, or with liquid or solid auxiliaries, such as water, benzyl alcohol, propylene glycol, polyalkylene glycols, vegetable oils, gelatin, starch, lactose and magnesium stearate. The preparations may be shaped into tablets, coated tablets, grains, pills or capsules, or they may occur in liquid form, such as solutions, emulsions or suspensions. Furthermore, they may be used in the form of suppositories. They may also contain the required auxiliaries, such as fillers, lubricants, preservatives and emulsifying agents, and are prepared in these forms by any method known per se. Per dosage unit they contain, for example, 1–20 mg of the active substance depending upon the way in which they are to be administered, as well as the nature and degree of the biological activity sought to be elicited. Thus, for example, the daily dosage may vary from 10–90 mg.

The compounds may also be prepared for external use by introducing them into a spray together with a suitable propellant and, if desired a solvent, further as a fine powder together with a suitable filler, and as a cream in combination with known auxiliaries.

The compound, according to the invention, may be isolated and applied in the form of its acid addition salts of the therapeutically acceptable acids, such as the inorganic acids, hydrocholoric acid, sulphuric acid, hydrobromic acid and phosphoric acid and organic acids, such as acetic acid and propionic acid, and substitution products thereof such as cyclohexyl propionic acid and phenyl propionic acid, tartaric acid, malic acid, citric acid, ascorbic acid, gluconic acid, mandelic acid, lactic acid, benzoic acid, fumaric acid, maleic acid, methane sulphonic acid, ethane sulphonic acid, succinic acid, aspartic acid, glutamic acid and sulfamic acid.

The following examples are illustrative of the invention:

EXAMPLE 1

Twenty grams of GB-94, 25 gm of starch and 97 gm of lactose are mixed together. To the mixture there is added a solution of 2 gm of gelatin in water while kneading. The obtained mixture is granulated, dried and mixed with 1 gm of magnesium stearate and 5 gm of talcum and pressed into tablets.

The tablets are then treated with a solution of shellac (1.5 mgm per tablet) in ethanol, next dried and further treated with an aqueous solution of 3.5 mgm of gelatin per tablet. Then the tablets are coated with talcum (3 mgm), starch (5 mgm) and sugar (280 mgm). The coated tablets are polished with a mixture of white wax (0.02 mgm) and carnauba wax (0.06 mgm per tablet). These tablets may be used as anxiolytic and neuroleptic preparations.

EXAMPLE 2

In order to establish that GB-94 has systematic and significant effects on human brain function, a single rising dose tolerance study was conducted with GB-94 utilizing therefor normal healthy volunteers and using the methods of quantitative pharmaco-EEG. The study was of the single blind type. After administration of an initial placebo medication, two subjects (both white; one male and one female; 23 and 20 years of age, respectively, both 70 kg in weight; the male 1.83 meters and the female 1.65 meters in height) were given GB-94 in two five-day intervals in a rising dose order (5 mg, 10 mg and 20 mg). EEGs were recorded and clinical investigations were conducted pre-drug (or placebo) and 1 and 3 hours after drug (or placebo) administration. In each time period, a 10-minute EEG (5 min. resting and 5 min. reaction time) was recorded. Right occipital to right ear EEG lead was recorded on paper chart as well as on analog type recorder (SP700).

CLINICAL RESULTS

Clinical evaluations were conducted using psychosomatic rating scale of side effects, a self-rating scale for sedation and transquilizing activity, a neurological examination and an interview.

Patient #1 (M.E.)

After Placebo: Patient had tachycardia before placebo but it disappeared after administration of the placebo. Three hours after administration, there was slight increase of drowsiness.

After 5 mg GB-94: One hour after administration, no changes were observed. Three hours after administration, there was slight sleepiness, but no other significant changes.

After 10 mg GB-94: One hour after administration there was no change. Three hours after administration, slight dryness of the mouth was reported but no other changes.

After 20 mg GB-94: One hour after administration, there was slight dryness of the mouth. Three hours after administration a slight increase in sleepiness was reported.

In summary, no significant clinical side effects and/or behavioral alterations were observed after any of the dosages of GB-94 with the exception of sleepiness.

Patient #2 (H.K.)

After Placebo: One hour after administration, no significant changes were observed. Three hours after administration, a disappearance of a burning sensation in stomach was reported with no other changes.

After 5 mg GB-94: One hour after administration a slight increase of headache, increase of appetite, slight increase of restlessness, increase of drowsiness and disappearance of irritability. Three hours after administration, no significant changes in comparison to one hour after the administration of the drug.

After 10 mg GB-94: One hour after administration there was no significant change. Three hours after administration a slight increase of euphoric feeling was observed.

After 20 mg GB-94: One hour after administration, there was a slight increase in drowsiness and sleepiness. Three hours after administration, no significant changes were observed or reported.

In summary, no noticeable side effects nor significant behavioral changes were observed after any of the dosages of GB-94 during the 3 hour period after the drugs administration excepting for drowsiness and euphoria.

COMPUTER EEG FINDINGS

The right occipital to right ear lead EEG recording was analyzed by a digital computer (PDP-12) using period analysis programs. The results indicated that:

After 5 mg GB-94: Whereas the mean values of the two subjects showed an increase of slow and fact activities and decrease of alpha frequencies in the primary wave measurements, the evaluation of a single subject demonstrated that the 16–20 cps, 20–26.6 cps and 26.6–40 cps bands increased during both 1-hour and 3-hour periods.

| | | VAP NO. | GB-94 5 mg., Phase 2 Resting | | | |
|---|---|---|---|---|---|---|
| | | | Pre-1 Hr. | | Pre-3 Hrs. | |
| | | | Period Mean | 2-Pre γ-Val | Period Mean | 3-Pre γ-Val |
| Z-C | 0.0–3.5 | 1 | −0.035 | −1.00 | −0.005 | −0.08 |
| | 3.5–7.5 | 2 | 0.035 | 7.00 | 0.045 | 0.82 |
| | 7.5–13.0 | 3 | −0.010 | −0.20 | −0.045 | −0.39 |
| | 13.0–20.0 | 4 | 0.010 | 1.00 | 0.0 | 0.0 |
| | 20.0–26.6 | 5 | 0.010 | 1.00 | 0.005 | 1.00 |
| | 26.6–40.0 | 6 | 0.0 | ****** | 0.0 | ****** |
| | 40.0–up | 7 | 0.0 | ****** | 0.005 | 1.00 |
| Z-C | AVG.FREQ. | 8 | 0.350 | 3.89 | 0.035 | 0.05 |
| Z-C | FREQ.DEV. | 9 | 0.540 | 0.67 | 0.960 | 2.00 |
| F-D | 0.0–10.0 | 10 | −0.045 | −1.80 | −0.035 | −7.00 |
| | 10.0–16.0 | 11 | −0.015 | −0.43 | −0.045 | −1.29 |
| | 16.0–20.0 | 12 | 0.015 | 3.00 | 0.030 | 3.00 |
| | 20.0–26.6 | 13 | 0.025 | 1.00 | 0.015 | 0.43 |
| | 26.6–40.0 | 14 | 0.015 | 0.60 | 0.15 | 0.60 |
| | 40.0–50.0 | 15 | −0.005 | −1.00 | 0.010 | 1.00 |
| | 50.0–up | 16 | 0.0 | ****** | 0.010 | 1.00 |
| F-D | AVG.FREQ. | 17 | 0.675 | 0.73 | 1.660 | 33.21+ |
| | AVG.AMP. | 18 | −5.255 | −1.18 | −0.600 | −0.09 |
| | AMP.VAR. | 19 | −0.520 | −0.23 | 1.965 | 2.95 |

+ = P < 0.05
* = P < 0.01
T—Test
Note:
******Indicates that T-statistic is undefined After 10 mg GB-94: The changes in CEEG measurements were not strong. A tendency to both slow and fast frequencies was noticeable.

After 20 mg GB-94: An increase of slow frequencies (0–3.5, 3.5–7.5 cps) in primary wave measurements during the 1st. hour (increase of 3.5–7.5 cps activity during the 3rd-hour recording) and a decrease of high frequency activities in both primary wave and first derivative measurements during the 3rd-hour recordings was seen.

| | | VAP NO. | GB-94 20 mg., Phase 2 Reaction Time | | | |
|---|---|---|---|---|---|---|
| | | | Pre-1 Hr. | | Pre-3 Hrs. | |
| | | | Period Mean | 2-Pre γ-Val | Period Mean | 3-Pre γ-Val |
| Z-C | 0.0–3.5 | 1 | 0.825 | 0.71 | 0.010 | −1.00 |
| | 3.5–7.5 | 2 | 0.000 | 1.00 | 0.025 | 1.67 |
| | 7.5–13.0 | 3 | −0.115 | −0.92 | 0.010 | 0.03 |
| | 13.0–20.0 | 4 | −0.015 | −3.00 | −0.015 | −3.00 |
| | 20.0–28.6 | 5 | 0.0 | ****** | −0.005 | −1.00 |
| | 26.6–40.0 | 6 | 0.0 | ****** | −0.005 | −1.00 |
| | 40.0–up | 7 | 0.005 | 1.00 | −0.005 | −1.00 |
| Z-C | AVG.FREQ. | 8 | −0.020 | −1.12 | −0.480 | −4.00+ |
| Z-C | FREQ.DEV. | 9 | 0.450 | 0.49 | −1.150 | −2.80 |
| F-D | 0.0–10.0 | 10 | −0.015 | −0.60 | 0.075 | 5.00 |
| | 10.0–16.0 | 11 | −0.025 | −1.00 | 0.0 | 0.0 |
| | 16.0–20.0 | 12 | 0.015 | 3.00 | −0.005 | −0.33 |
| | 20.0–26.6 | 13 | −0.005 | −1.00 | −0.015 | −1.00 |
| | 26.6–40.0 | 14 | 0.015 | 1.00 | −0.026 | −5.00 |
| | 40.0–50.0 | 15 | 0.010 | 1.00 | −0.005 | −1.00 |
| | 50.0–up | 16 | 0.015 | 1.00 | −0.005 | −1.00 |
| F-D | AVG.FREQ. | 17 | 1.380 | 0.80 | −1.840 | −2.36 |
| | AVG.AMP. | 18 | −0.640 | −0.05 | 9.140 | 1.10 |
| | AMP.VAR. | 19 | −5.735 | −1.30 | −3.810 | −1.01 |

+ = P < 0.05
* = P < 0.01
T—Test
Note:
******Indicates that T-statistic is undefined In summary, the increase of activities, particularly in the frequency range of 20–40 cps in the computer EEG analysis (in one subject), resembled the alterations observed after administration of benzodiazepine anxiolytics (minor tranquilizers) such as diazepam. Accordingly, it can be assumed that GB-94 in low dosages will have clinical effects similar to those of the anxiolytic compounds.

The CEEG alterations induced by 20 mg GB-94 (increase of slow waves and decrease of fast activities) resembled the CEEG profiles of neuroleptic compounds with sedative properties. Therefore, GB-94 will have the therapeutic effects similar to those observed for the neuroleptic (major tranquilizer) compounds.

EXAMPLE 3

In order to determine whether GB-94 has any neuroleptic (major tranquilizer) properties, two studies were conducted in schizophrenic patients:

Study #1;

Ten male hospitalized schizophrenic patients in an age range of 22–44 years (mean 31.8 years) having no abnormal physical or laboratory findings were included in this study (3 of the subjects were unskilled, 5 semi-skilled and 2 of managerial status; 7 patients were single, 2 married and 1 divorced; 6 patients had schizophrenic reactions, simple type, 3 had paranoid schizophrenia and 1 was diagnosed as chronic undifferentiated type). The length of illness of the patients ranged from 1–12 years (mean 4.7 yrs.).

Following 3–10 days of placebo administration, the patients received one or two single doses of oral placebo medication; then in 3- to 7-day intervals, GB-94 was given in a single rising dose order (oral administration) of 25 mg, 50 mg, 75 mg; following this another placebo, and following placebo, GB-94 again in doses of 100 mg, 150 mg and 200 mg. Four patients were unable to complete this study. In one patient following the administration of 100 mg an acute vaso-vegatative syndrome was observed two hours after the drug was administered. In another patient after 150 mg, an increase of uric acid was observed. A third patient was dropped from the study after 100 mg because this patient reported suicidal thoughts. The fourth patient left the hospital after 100 mg and was therefore dropped from the program. The other six patients received GB-94 in up to 200 mg single oral doses according to the protocol and they completed the study without any serious problems being encountered.

Evaluation of Individual Patients

Patient #1

After 25, 50 and 75 mg GB-94, the patient evidenced sleepiness and drowsiness. After 100 mg, the patient had slight difficulty breathing, reported feeling cold and shaky, nausea and vomiting, was restless, fatigued, drowsy and sleepy. He was frightened and evidenced anxiety. He was very weak, dizzy, appeared drunk and sluggish. He perspired and reported feelings of faintness. This state began about 2 hours after the administration of 100 mg GB-94 and lasted for 1 ½ hours. After the acute state, he was irritated and angry. Although this state was not very severe, it was decided not to further increase the drug in this patient and to drop him from the study.

Patient #2

Before drug administration, this patient was generally sleepy, drowsy, restless and dizzy. After 75, 100 and 150 mg of GB-94, these symptoms slightly increased. No marked side effects were observed after any of the dosages, including 200 mg.

Patient #3

Three hours after 75 mg this patient demonstrated restlessness, anxiety, weakness, dizziness and irritability. Three hours after 100 mg he was drowsy, sleepy, weak, dizzy, restless, irritable and reported feelings of faintness. This patient was mildly ill before the study. His symptoms increased after 100 mg single dose and included conceptual disorganization, suspiciousness, hostility, uncooperativeness, and unusual thought content. Before the study was completed, this patient left the hospital and tried to commit suicide by throwing himself in front of a truck and was as a result slightly injured. He was dropped from the study. After treatment for a period of 3 weeks with neuroleptic medication, he showed remarkable improvement and was discharged from the hospital.

Patient #4

This patient had various psychosomatic disturbances such as restlessness, dizziness, drunkenness, weakness, and anxiety. Following administration of dosages of 100 mg and 150 mg of GB-94, these symptoms increased slightly. Three hours after 200 mg GB-94 he showed increased perspiration, difficulty in breathing, nausea, restlesness, weakness, and faintness, and complained of a burning sensation in the stomach. These symptoms completely disappeared within a period of 2 to 3 hours after the test period.

Patient #5

This patient evidenced sleepiness, weakness, dizziness, drunkenness, and euphoria following receipt of 25 mg and 50 mg of GB-94. Slight speech disturbance, vomiting, itching, drowsiness, weakness, dizziness, drunkenness, and fainting were seen after 75, 100 and 150 mg. These symptoms occurred about 1 ½ hours after drug administration and lasted for up to 3 hours. At the predrug evaluation this patient had non-systematized persecutory delusions, absurdity, inability to realize events, free-floating anxiety, attacks of aggression and hostility and suicidal compulsions. He showed slight improvement with the 50 mg single dose. With 75, 100 and 150 mg, no further improvement in symptomatology was observed. Because he evidenced no benefit from the drug and because of the side effects the last dosage of 200 mg was not given.

Patient #6

After doses of 25, 50 and 75 mg of test compound, this patient showed only slight sleepiness. Two to three hours after administration of 100 mg, sleep disturbances, difficulty in breathing, cold and shaky feeling, burning sensation in stomach, abdominal pain, nausea and vomiting, anorexia, burning sensation in hands, fatigue, drowsiness, anxiety, increased perspiration, faintness, weakness, dizziness and drunkenness were observed. In spite of the increase of the single dosages to 150 and 200 mg, no side effects except for slight sleepiness were observed.

Patient #7

Except for slight drowsiness, sleepiness, and sometimes dizziness, this patient did not show any side effects up to the 200 mg single dose. The study could be completed without any problems.

Patient #8

Except for slight weakness and tiredness after 50 mg and euphoria after 75 mg, this patient showed no side effects and the 200 mg single dose of GB-94 could be given without encountering any problems.

Patient #9

This patient demonstrated slight fatigue, drowsiness, sleepiness, weakness, and diziness with 50 mg, but no side effects after 75 and 100 mg. He left the hospital and therefore did not complete the study.

Patient #10

After almost every dosage of GB-94, this patient showed slight sleepiness, fatigue, weakness and drunkenness. After 100 mg he had a burning sensation in the stomach, nausea, perspiration and fainting feeling. After 200 mg, he showed symptons of perspiration, sleep disturbance, fatigue, drowsiness, weakness, dizziness, drunkenness, and fainting. These symptoms started 1 to 2 hours after oral administration of the GB-94 and lasted for 1 to 2 hours. At the beginning of the treatment, and particularly after the 200 mg single dose, this patient showed much improvement. However, this lasted only for a short period and he had a relapse. The study was completed in this patient without any problems.

SUMMARY AND CONCLUSION

After 24 days of the GB-94 study period, utilizing the Global Evaluation Rating Scale, 6 patients showed improvement (1 marked improvement, 3 moderate improvement, 2 slight improvement), 2 patients showed two points worsening, and 2 patients could not be rated because they were dropped from the study.

According to the Modified Brief Psychiatric Rating Scale, the total score decreased in 7 patients, and increased in 3 patients. The improved symptoms included anxiety, conceptual disorganization, mannerism and posturing, blunted affect, insight, judgment, elated mood and euphoria. However, hostility increased. By a sign test, there was a significant increase in motor retardation, but a decrease in a cluster of items relating to disorganized thinking (conceptual disorganization, attention, concentration, insight, judgment, inappropriate and silly affect).

After the administration of only a single dose of GB-94, one subject showed marked improvement, 3 moderate and 2 slight improvement. Two patients could not be evaluated and were dropped from the program (one patient was dropped from the study because he had left the hospital). Two subjects showed slight worsening of their symptomatology in the course of the study. Since all of the subjects were on high dosages of neuroleptic agent before the GB-94 trial, the worsening might be due to lack of adequate dosage of the routine neuroleptic treatment. One patient could not be evaluated since he was dropped from the program in the early phase of the study.

No serious clinical side effects or laboratory changes were observed in this study. In the majority of patients, however, marked sedation associated with weakness, faintness, dizziness and increased perspiration were observed. This was dose related and was basically observed after 100 mg dosages of the GB-94.

Several of the patients complained about nausea, vomiting, burning sensation in stomach, and difficulty in breathing. All of these side effects commenced 1 to 2 hours after drug administration and lasted for 1 to 3 hours, appearing spontaneously. Except for a slight increase of the SGPT and SGOT in some of the patients, no significant laboratory findings were observed.

Study #2

In order to determine whether GB-94 has any therapeutic effects when administered to schizophrenic patients, a single-blind study was carried out in a group of 10 hospitalized male patients having an age range of 20-44 years (mean 30.3 years). A respective schizophrenic diagnostic subgroup included 4 hebephrenic patients, 4 patients with paranoid reactions, 1 catatonic patient, and 1 chronic undifferentiated type schizophrenic. Except for two patients who were not treated systematically, all of the patients had previously received psychotropic drug treatment (Haloperiodol and/or Prolixin and/or Thioproperazine) and/or electroconvulsive treatment without any significant benefit being observed. The patients were treated for a total of four weeks with a fixed daily dosage of Mianserin. All of the patients with one exception, received 100 mg daily (50 mg B.I.D.) of GB-94 during the first week of treatment, all received 150 mg daily (50 mg T.I.D.) during the second week, 200 mg daily (50 mg Q.I.D.) during the third week, and 300 mg daily (100 mg T.I.D.) during the fourth week of treatment. The total GB-94 dosage received by the patients in the four weeks of treatment ranged from 5,250–5,550 mg of drug.

Evaluation of Individual Patients

Patient #1

This patient was severely ill during the GB-94 chronic dose tolerance study. His main symptoms were polymorphic non-systematized macromaniacal delusions, hallucinatory behavior, psychomotor retardation, grandiosity, and unusual thought content. He had moderately severe impaired insight and judgment. He showed a slight overall clinical improvement in the second week. Moderate improvement was observed in the overall syndrome, the paranoid syndrome was characterized by non-systematized delusions of grandiosity and auditory hallucinations.

Patient #2

This patient had been markedly ill at the time the study was instituted. His target signs and symptoms included fear of being accused as a homosexual and persecutory delusions and auditory hallucinations related thereto. He had moderate anxiety. In the second week of treatment, he showed better social adaptation and was less preoccupied with the symptoms and fears. The delusions and hallucinations also decreased in intensity. In the fourth week, all of his symptoms improved moderately. He received a total of 5,250 mg GB-94 over 30 days.

Patient #3

This patient was moderately ill and had an undifferentiated type of schizophrenia, displaying anxiety, lack of enthusiasm, motor retardation, tension, emotional withdrawal and disinterest. During the treatment with GB-94 no improvement but rather a slight worsening of his condition was observed. He received a total of 5,250 mg GB-94.

Patient #4

This patient was markedly ill with target symptoms of non-systematized persecutory paranoid delusions, silly infantile behavior, inability to realize awareness, and lack of insight. He had severely impaired judgment. The patient showed a very slight improvement in the second week which did not, however, change the status of the care received by the patient. In the third and fourth weeks, he showed very marked improvement with a disappearance of all of his symptoms. His social adaptability also improved greatly. He still had a slight paranoid manner of thought when the study ended. He received a total of 5,250 mg GB-94.

Patient #5

This patient was moderately ill when he was hospitalized and at the time he was included in this study. His main symptoms were absurdity, "word salad," lack of insight, inability to realize events, indifference, stereotyped movements, and slight choreoform movements in both hands. Although he did not show any psychosomatic side effects during the treatment with GB-94, all his psychotic symptoms increased and he was evaluated as being a most extremely ill patient. We considered him as very much worsened after a total dosage of 5,250 mg GB-94.

Patient #6

This patient was among the most extremely ill patients when he was accepted for the study. His main symptoms were absurdity, indifference, inability to realize awareness, irritability, aggressiveness, uncooperativeness, and masturbation without a sense of embarrassment. He had lack of insight and judgment, was depersonalized, and had hallucinatory behavior. After two weeks of treatment, he showed no improvement at all and towards the fourth week his symptoms increased and he became worse. This patient received a total dosage of 5,550 mg GB-94.

Patient #7

This patient was severely ill having as his main symptoms complete indifference, catatonic behavior, mutism, autism, and refusal to eat. The patient became worse during the first 10 days of the GB-94 treatment and had to be dropped from the study. In the 12 days of GB-94 treatment, this patient received a total of 1,450 mg GB-94 (daily dosages of 100–150 mg).

Patient #8

This patient was severely ill with main symptoms of absurdity, mannerism, euphoria, slight perplexity, lack of insight, inability to realize events, auditory hallucinations, poor communication, and silly behavior. During the four weeks of GB-94 treatment, he did not show any improvement but rather worsened and was included among the most extremely ill of patients. This patient received a total dosage of 5,550 mg GB-94.

Patient #9

This patient was markedly ill having as his main symptoms unsystematized persecutory delusions, absurdity, ambivalence, hallucinatory behavior, emotional withdrawal, and impaired insight and judgment. In the fact two weeks of the treatment, he showed no change at all. After four weeks of treatment with GB-94, he showed much improvement. His absurdity and ambivalence as well as delusions disappeared. Only very mild auditory hallucinations remained. This patient received a total of 5,250 mg GB-94.

Patient #10

This patient was mildly ill with his main symptoms consisting of blunted affect, uncooperativeness, moderate inability to realize events, and lack of insight. He had slight mannerisms. Within two weeks he showed moderate improvement and his affect became normal. At the end of the four weeks of treatment he had very few symptoms of psychosis.

SUMMARY AND CONCLUSION

According to the Global Behavioral Rating Scale, 5 of the 10 patients showed slight to marked improvement in total psychopathology, 4 showed deterioration and 1 showed no change. The evaluation of the Modified Brief Psychiatric Rating Scale demonstrated that the response of the patients demonstrated improvement in somatic concern, emotional withdrawal, conceptual disorganization, hostility, tension, suspiciousness, motor retardation, inappropriateness, and disinterest. During GB-94 treatment, no serious clinical side effects, labortory abnormalities, EKG or eye findings were observed.

EXAMPLE 4

In order to determine whether GB-94 has any anxiolytic (minor tranquilizer) properties, an open study was conducted in a group of non-hospitalized patients having anxiety syndromes. Nine female patients and 1 male patient having an age range of 21–56 years (mean 32.8 years) with moderate to severe anxiety, but having no physical abnormalities, were included in this study (7 of the 10 patients were married, 1 single and 2 divorced; professionally, 1 patient was skilled, 5 semi-skilled, 1 clerical and 3 unskilled; 6 patients were diagnosed as neurotic and 4 neurasthenic). GB-94 was given during the first seven days of the treatment in a fixed dosage schedule (5 mg B.I.D.) increasing to 50 mg daily in the seventh day of treatment and in Doctor's Choice dosages in the 8th and 21st day of treatment, but never receiving more than 70 mg daily. Patients who completed the study received the maximum total dosage of 845 mg GB-94 and minimum dosages of 655 mg.

Despite the small number of patients, the statistical evaluation of the Global Rating Scale demonstrated a significant improvement for the group during the first and third weeks of the treatment. The clinical evaluation according to the Hamilton Anxiety Rating Scale demonstrated that tension, difficulty in respiration, insomnia, anxious mood, agitation, and restlessness showed noticeable improvement. Clinical side effects evaluation according to the Psychosomatic Rating Scale also demonstrated that difficulty in breathing was significantly improved based on all three statistical evaluations. Except for drowsiness, sleepiness and fatigue, no unpleasant side reactions were observed during GB-94 treatment. This study indicated that GB-94 indeed has anxiolytic (minor tranquilizer) properties.

EXAMPLE 5

Five grams of GB-94 and 1 gram of chlorocresol are dissolved, while heating in 100 grams of water. Then a solution is made by melting together 12.5 grams of spermaceti, 12 grams of white wax and 56 grams of liquid paraffin. Next, the latter solution is added to the former and stirred until the mixture has cooled down. A pharmaceutical cream is thereby obtained which can then be employed by applying the same to broken areas of the skin or to the skin where an exceedingly slow diffusion of the active ingredient is desired, though this method is least effective where prolonged therapy is indicated.

EXAMPLE 6

A pharmaceutical preparation suitable for injection is made by dissolving the following ingredients in water and sterilizing the obtained solution:

|  | Mgm |
| --- | --- |
| Compound GB-94 | 1.0 |
| Sodium chloride | 8.5 |
| Methyloxybenzoate | 0.85 |
| Propyloxybenzoate | 0.15 |
| Distilled water to 1.0 ml | |

This preparation is an active anxiolytic (minor tranquilizer) and antipsychotic (major tranquilizer or neuroleptic).

Summary of Computer EEG and Clinical Findings

According to the initial pharmacological data, GB-94 was found to be less depressant than Cyproheptadine when evaluated for the potentiation of duration of hypnosis, on behavioral changes, and on the electroencephalographic pattern after both drugs (Basic Data Report on GB-94 by Organon, dated Nov. 15, 1968). According to "pilot" pharmacological studies, GB-94 was found to be less toxic and less depressing on the central nervous system then Cyproheptadine. It was felt that "this property, if confirmed in clinical trials, would be an obvious advantage of GB-94" for use as an antiallergic drug. In the same report, it was summarized that "from its pharmacological activity, the clinical effectiveness of GB-94 might be considered in allergic conditions such as some kind of asthma, urticaria, pruritus, exema, high fever, etc. Moreover, it could be indicated in other conditions in which serotonin is assumed to play an important role such as in carcinoid syndrome, serotonin flashing (dumping syndrome) and migraine."

After the applicant's EEG and clinical prediction of psychotropic properties for GB-94, subsequent animal pharmacology studies were conducted. In summary of data on animal pharmacology, it was stated that "following the demonstration of psychoactivity in man GB-94 was subjected to further animal psychoactive profiling. GB-94 was then found to be active in many tests intended to detect CNS activity" (Summary of Basic Data on Organon's GB-94, April 1972). As a general conclusion, it was stated "that the profile of CNS actions in animals and of biochemical effects do not allow GB-94 to be classed as a member of any of the known classes of psychotropic drugs."

In contrast to animal data, the results of applicant's human studies indicate that GB-94 indeed has noticeable psychotropic properties. According to the quantitative pharmaco-EEG study, in low dosage (5 mg), GB-94 produced, at least in one subject, a CEEG profile which is "typical" for anxiolytic (minor tranquilizer) CEEG profiles (Itil, T. M. Electroencephalography and Pharmacopsychiatry, Freyhan, F. A., et al (Ed.). Clin. Psychopharm., Mod. Probl. of Pharmacopsych. Vol. 1, Basel/New York: Karger, 1968, pp. 163-194; Itil, T. M. Quantitative Pharmaco-EEG in assessing new anti-anxiety agents, Vinar, O. et al (Eds.), Advances in Neuro-Psychopharmacology, North Holland Publ. Co/Amsterdam, 1971, pp. 199-209).

The CEEG profiles after 20 mg GB-94 was characterized by an increase in slow waves and a decrease of fast activities in both the primary wave and first derivative measurements. These kind of CEEG profiles were described by applicant as "typical" for neuroleptics (major tranquilizers) (Itil, T. M., Electroencephalography and pharmacopsychiatry, Freyhan, F. A. et al (Eds.), Clin. Psychopharm. Mod. Probl. of Pharmacopsych. Vol. 1, Basel/New York: Karger, 1968, pp. 163-194).

The clinical trials in patients having anxiety syndromes clearly demonstrated that GB-94 has in relatively low dosages (5-50 mg) anxiolytic (minor tranquilizer) properties, thus confirming the prediction which was made following the results of the quantitative pharmaco-EEG study. In therapeutic dosages, GB-94 did not produce any unpleasant side effects (except some sedation which was cleared up three days following the onset of treatment). Abnormal laboratory findings were not observed in this study.

The single and multiple rising dose studies established the therapeutic effect of GB-94 in schizophrenic symdromes. Accordingly, the neuroleptic (major tranquilizer) properties of GB-94 were discovered as a result of the quantitative pharmaco-EEG study and were confirmed by the clinical observations and statistical analysis.

In conclusion, it was established that GB-94 has a therapeutic effect in symptoms of emotional withdrawal, conceptual disorganization, hostility, suspiciousness, hallucinatory behavior, tension and motor retardation of psychotic patients, particularly in schizophrenics. Furthermore, it was determined that symptoms such as anxious mood, insomnia, nervousness, worried behavior, lack of desire for eating and drinking, loss of appetite, disturbances of the cardiovascular system, disturbances of respiratory system, and disturbances of the autonomic system of patients having neurotic and neurasthenic syndromes were significantly improved. Except for drowsiness, sleepiness and fatigue, no unpleasant side reactions or abnormal laboratory findings were found in the patients having anxiety syndromes during their treatment with GB-94.

While the above described dosages are the preferred dosages, dosages of 5-300 mg are also suitable. Single oral dosages of 100 mg or more generally will produce marked sedation and possible side effects such as weakness, faintness, dizziness, increased perspiration, nausea, vomiting and a burning senation in stomach. Ideal dosages are therefore about 5-50 mg., preferably 5-20 mg. daily when GB-94 is employed as an anxiolytic. GB-94 has, however, been administered in amounts of up to 300 mg. daily in schizophrenics without observing unusual and/or serious side effects. GB-94 is preferably administered orally using the tablet form of administration and by administrating the drug in three daily divided dosages.

I claim:

1. A method of treating psychiatric patients exhibiting psychotic behavior, and in particular a schizophrenic symdrome which comprises administering to such patient a therapeutically-effective amount of a compound having the formula

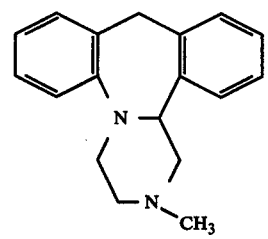

2. A method of treating psychiatric patients exhibiting symptoms of anxiety, particularly when associated with neurotic or neurasthenic disorders comprising administering to such patient a therapeutically effective amount of a compound having the following formula

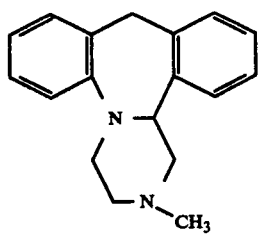

3. A method as defined in claim 1, wherein said compound is administered in amounts of about 5–300 mg daily.

4. A method as defined in claim 2, wherein said compound is administered in amount of about 5–50 mg daily.

5. A method as defined in claim 1, wherein said compound is administered orally.

6. A method as defined in claim 1, wherein said compound is administered orally in tablet form.

7. A method as defined in claim 1, wherein said compound is administered orally in form of its solution, suspension or dispersion, in a suitable pharmaceutical liquid vehicle.

8. A method as defined in claim 1, wherein said compound is in the form of a tablet, capsule, pellet, dragee, pill, powder or granular substance.

9. A method as defined in claim 1, wherein said compound is administered parenterally in the form of injectable solution.

10. A method as defined in claim 1, wherein said compound is administered in long-acting form.